United States Patent
Kantzer et al.

(10) Patent No.: US 10,995,058 B2
(45) Date of Patent: May 4, 2021

(54) PROCESS FOR MANUFACTURING HYDROXYETHYL ETHYLENE AMINES

(71) Applicant: NOURYON CHEMICALS INTERNATIONAL B.V., Arnhem (NL)

(72) Inventors: Eike Nicolas Kantzer, Uddevalla (SE); Karl Fredrik Lake, Södertälje (SE); Antoon Jacob Berend Ten Kate, Arnhem (NL); Michiel Jozef Thomas Raaijmakers, Deventer (NL); Rens Veneman, Deventer (NL); Ina Ehlers, Stenungsund (SE); Michael Bertil Einar Sarning, Gothenburg (SE); Hendrik Van Dam, Ede (NL); Rolf Krister Edvinsson, Partille (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/468,496

(22) PCT Filed: Dec. 12, 2017

(86) PCT No.: PCT/EP2017/082392
§ 371 (c)(1),
(2) Date: Jun. 11, 2019

(87) PCT Pub. No.: WO2018/108888
PCT Pub. Date: Jun. 21, 2018

(65) Prior Publication Data
US 2020/0071260 A1     Mar. 5, 2020

(30) Foreign Application Priority Data
Dec. 15, 2016   (EP) .................................. 16204357

(51) Int. Cl.
*C07C 213/08*    (2006.01)
(52) U.S. Cl.
CPC .................................. *C07C 213/08* (2013.01)
(58) Field of Classification Search
None
See application file for complete search history.

(56) References Cited

U.S. PATENT DOCUMENTS

| | | | |
|---|---|---|---|
| 2,448,767 A | 9/1948 | Carlson et al. | |
| 3,383,417 A | 5/1968 | Lichtenwalter | |
| 3,682,919 A | 8/1972 | Johansson et al. | |
| 4,044,053 A | 8/1977 | Brennan et al. | |
| 4,503,250 A | 3/1985 | Herdle | |
| 5,225,599 A * | 7/1993 | King | C07C 213/08 564/480 |
| 6,534,441 B1 | 3/2003 | Bartley et al. | |
| 7,700,806 B2 | 4/2010 | van Cauwenberge et al. | |
| 8,563,778 B2 | 10/2013 | Hanson et al. | |
| 9,353,044 B2 | 5/2016 | King et al. | |
| 2009/0240084 A1 | 9/2009 | Van Cauwenberge et al. | |
| 2012/0232309 A1 | 9/2012 | Schaub et al. | |
| 2014/0179931 A1 | 6/2014 | Gupta et al. | |
| 2019/0031597 A1 | 1/2019 | Edvinsson et al. | |
| 2019/0039993 A1 | 2/2019 | Edvinsson et al. | |
| 2019/0039994 A1 | 2/2019 | Edvinsson et al. | |
| 2019/0047971 A1 | 2/2019 | Edvinsson et al. | |
| 2019/0308930 A1 | 10/2019 | Kantzer et al. | |
| 2020/0131136 A1 | 4/2020 | Ten Kate et al. | |
| 2020/0165187 A1 | 5/2020 | Ten Kate et al. | |
| 2020/0165207 A1 | 5/2020 | Kantzer et al. | |
| 2020/0165212 A1 | 5/2020 | Raaijmakers et al. | |

(Continued)

FOREIGN PATENT DOCUMENTS

| | | |
|---|---|---|
| CA | 2801109 A1 | 12/2011 |
| CN | 102167682 A | 8/2011 |

(Continued)

OTHER PUBLICATIONS

STN abstract of King et al. Patent (U.S. Pat. No. 5,225,599) (Year: 1993).*
Applicant letter to ISA concerning earlier search ("PCT Direct") (Dec. 12, 2017) in EP Application No. 16204362.4.
English-Language Machine Translation CN 103333323 A (2013) (Year: 2013).
English-Language Machine Translation JP 2815477 B (1998) (Year: 1998).
English-Language Machine Translation JP 2008002018 A (2008) (Year: 2008).
English-Language Machine Translation JP 2008019520 A (2008) (Year: 2008).
English-Language Machine Translation WO 2017125358 A (2017) (Year: 2017).
CAS Abstract WO2011/151268 (2011) (Year: 2011).
CAS Abstract WO 2017125358 (2017) (Year: 2017).
CAS Abstract Ethylene Glycol (1984) (Year: 1984).

(Continued)

*Primary Examiner* — Sudhakar Katakam
*Assistant Examiner* — Jennifer C Sawyer
(74) *Attorney, Agent, or Firm* — Lorenz & Kopf, LLP

(57) ABSTRACT

A process for preparing hydroxyethyl ethylene amines and/or ethylene urea derivatives thereof includes reacting monoethylene glycol with an amine-functional compound having at least two —NH— units, of which at least one is selected from the group of primary amine groups and cyclic secondary amine groups, in the presence of a carbon oxide-delivering agent. The amine-functional compound includes at least one —NH—CH2-CH2-NH— unit, wherein one or more —NH—CH2-CH2-NH— units in the amine-functional compound may be present in the form of piperazine moieties or ethylene urea moieties. The molar ratio of amine-functional compound to monoethylene glycol is in the range of 0.2:1 to 1.5:1 and the molar ratio of carbon oxide-delivering agent to —NH—CH2-CH2-NH— units in the amine-functional compound is at least 0.5:1. The process allows the conversion of monoethylene glycol into ethanol amines in the absence of metals-containing catalysts and without using ammonia.

15 Claims, No Drawings

(56) References Cited

U.S. PATENT DOCUMENTS

| | | |
|---|---|---|
| 2020/0199060 A1 | 6/2020 | Ten Kate et al. |
| 2020/0207701 A1 | 7/2020 | Veneman et al. |

FOREIGN PATENT DOCUMENTS

| | | |
|---|---|---|
| CN | 103333323 A | 10/2013 |
| CN | 103333323 B | 9/2015 |
| EP | 0 450 709 A1 | 10/1991 |
| JP | 2815477 B | 10/1998 |
| JP | 2008002018 A | 1/2008 |
| JP | 2008019520 A | 1/2008 |
| WO | 91/15458 A1 | 10/1991 |
| WO | 2011151268 A1 | 12/2011 |
| WO | 2017125358 A1 | 7/2017 |
| WO | 2018/108890 A1 | 6/2018 |
| WO | 2018108888 A1 | 6/2018 |

OTHER PUBLICATIONS

CAS Abstract JP 2008002018 (2008) (Year: 2008).
CAS Abstract JP 2008019520 (2008) (Year: 2008).
European Search Report issued in the counterpart European Application No. 16204357.4 dated Jun. 26, 2017.
Notification of Transmittal of the International Search Report and the Written Opinion of the International Searching Authority, or the Declaration from the International Bureau of WIPO for International Application No. PCT/EP2017/082392 dated Feb. 12, 2018.
Database WPI 1-12, Week 201410, Thomson Scientific, London, GB;AN 2013-W87652-& CN 103 333 323 A (Wuhan Keda Marble Protective Materials), Oct. 2, 2013, abstract, paragraph [0042] ; claim 1, XP002770988.
Schweitzer, Ethyleneurea. II. Syntheses From Ethylene Glycol or Ethanolamine and Urea (or Carbon Dioxide and Ammonia) Journal Organic Chemistry 1950, pp. 475-480.

* cited by examiner

PROCESS FOR MANUFACTURING HYDROXYETHYL ETHYLENE AMINES

This application is a national stage filing under 35 U.S.C. § 371 of PCT/EP2017/082392, filed Dec. 12, 2017, which claims priority to European Patent Application No. 16204357.4, filed Dec. 15, 2016, the contents of which are each incorporated herein by reference in their entireties.

The present invention pertains to a method for manufacturing hydroxyethyl ethylene amines using a specific starting material.

Hydroxyethyl ethylene amines find application in chemical processes, as solvent or as reactant. For example, aminoethyl ethanolamine or AEEA is an organic base used in the industrial manufacture of fuel and oil additives, chelating agents and surfactants.

Various processes for manufacturing hydroxyethyl ethylene amines have been described.

For example, U.S. Pat. No. 3,383,417 describes the manufacture of aminoethyl ethanolamine by reaction of monoethanolamine with itself in the presence of a catalyst comprising nickel, copper, and a minor amount of chromium oxide, manganese oxide, molybdenum oxide and thorium oxide.

U.S. Pat. No. 7,700,806 describes a process for preparing ethylene amines and ethanol amines by hydrogenative amination of monoethylene glycol and ammonia in the presence of a catalyst. The process is carried out in two stages, wherein in the first stage the amination is carried out over a hydroamination catalyst to a monoethylene glycol conversion of not more than 40%, and in the second stage the reaction is carried out over a supported catalyst comprising ruthenium and cobalt, with a specific particle shape.

U.S. Pat. No. 2,448,767 describes reacting ethylene carbonate with amine compounds to form hydroxyethyl amine compounds, e.g., by reacting aniline with ethylene carbonate.

Monoethylene glycol, also known as 1,2-ethanediol, is an attractive starting material in the chemical industry, also because it can be derived from renewable resources. EP 450 709 describes the preparation of ethylene amines and hydroxyethyl ethylene amines from alkylene glycol (which preferably is ethylene glycol) in a condensation reaction using a condensation catalyst selected from a Group IVB metal, oxide, a Group VIB metal-containing substance and a promoted condensation catalyst.

There is need in the art for a process which allows the conversion of monoethylene glycol into ethanol amines which can be carried out in the absence of metals-containing catalysts, and without using ammonia. It is preferred for such a process to have a high yield. The present invention provides such a process.

The invention pertains to a process for preparing hydroxyethyl ethylene amines and/or ethylene urea derivatives thereof comprising the step of reacting monoethylene glycol with an amine-functional compound comprising at least two —NH— units of which at least one is selected from the group of primary amine groups and cyclic secondary amine groups, the amine-functional compound comprising at least one —NH—CH2-CH2-NH— unit, wherein one or more —NH—CH2-CH2-NH— units in the amine-functional compound may be present in the form of piperazine moieties or ethylene urea moieties, in the presence of a carbon oxide-delivering agent, wherein the molar ratio of amine-functional compound to monoethylene glycol is in the range of 0.2:1 to 1.5:1 and the molar ratio of carbon oxide-delivering agent to —NH—CH2-CH2-NH— units in the amine-functional compound is at least 0.5:1.

It is noted that U.S. Pat. No. 4,503,250 describes a process for preparing predominantly linear polyalkylene polyamines by reacting ammonia or an alkylene amine compound having two primary amine groups with an alcohol or an alkanol amine in the presence of a derivative of carbonic acid at a temperature at which the reaction will proceed under pressures sufficient to maintain the reaction mixture in the liquid phase. This reference states that it is possible to use alcohols. However, all examples make use of ethanolamine compounds, specifically monoethanolamine, diethanolamine and aminoethylethanolamine. The only di-alcohol compound is diethanolamine (DEA), which is reacted with urea and only results in the formation of trace amounts (0.7 wt. %) of L-TETA. It mainly results in the conversion of the ethanol group into an amine group, which is not the aim of the present invention. Further, this document indicates that the amount of CO is not critical. The compound is regarded as a catalyst. This can also be seen from the very low amounts used in the examples. In particular, in all examples where carbon dioxide is added in the form of ethyleneurea, the molar ratio of CO to —NH—CH2-CH2-NH— group is 0.25:1 or lower. Further, this reference is directed to the manufacture of polyalkylene polyamines and not to the manufacture of hydroxyethyl ethylene amines.

It has been found that the process according to the invention makes it possible to obtain hydroxyethyl ethylene amines and derivatives thereof via a process which makes use of an attractive starting material, with relatively high yield, without having to use ammonia or metal-containing catalysts. Further advantages of the process according to the invention and specific embodiments thereof will become apparent from the further specification.

The present invention will be discussed in more detail below.

Monoethylene glycol is used as starting material. This compound can be provided as such, or at least in part in the form of a CO adduct, e.g., in the form of the cyclic ethylene carbonate, or in the form of a linear adduct such as HO—CH2-CH2-O—C(O)—O—CH2-CH2-OH.

Carbon oxide-delivering agents suitable for use in the present invention are compounds which are able to provide carbonyl groups under reaction conditions. Organic compounds in which a carbonyl group is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts that can be converted, in some embodiments in situ in the process of the invention, into their non-ionic counterparts, for example into linear and cyclic carbamate or urea compounds. Preferably, when such ionic compounds are used in the present invention, they are organic hydrocarbon-based carbonate or bicarbonate salts. Preferably, the organic compounds that are suitable for use as carbon oxide-delivering agents are those wherein alkylene is ethylene. The carbon oxide-delivering agent can be present in the process in the same molecule as the amine-functional or the monoethylene glycol compound.

It is preferred for the carbon oxide-delivering agent to be such that it does not provide additional organic compounds to the reaction mixture other than monoethylene glycol and the amine-functional compound.

Accordingly, preferably, the carbon oxide-delivering agent used in the present invention includes carbon dioxide, adducts of carbon dioxide with monoethylene glycol, such as the compounds discussed above, and adducts of carbon dioxide with amine-functional compounds.

Examples of suitable carbonyl adducts of amine-functional compounds include ethylene urea (EU), diaminoethylene urea (DAEU), which is the linear adduct of two ethylene diamine molecules, the cyclic urea derivative of diethylene triamine (UDETA), and cyclic urea derivatives of triethylene tetramine, such as the cyclic urea derivative of triethylene tetramine, with the carbonyl group added to the terminal NH2-CH2-CH2-NH moiety (U1TETA) and the cyclic diurea additive of triethylene tetramine (DUTETA).

Examples of carbon oxide delivering agents include:

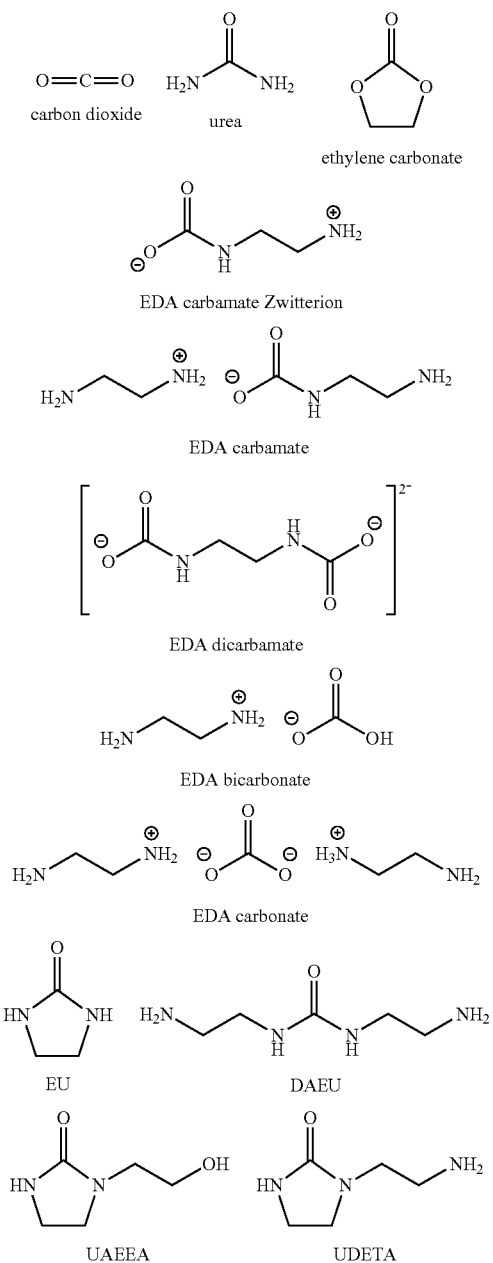

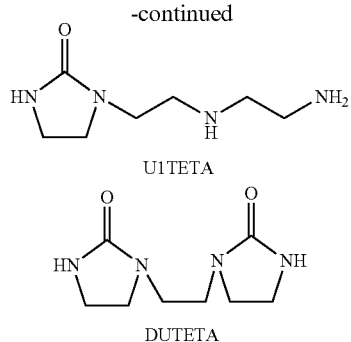

The use of a carbon oxide-delivering agent selected from the group of carbon dioxide, ethylene carbamate, and ethylene urea (EU) and other urea adducts of amine compounds may be particularly preferred. Of course, combinations of the various types of carbon oxide-delivering agents may be applied, if so desired.

The present invention makes use of an amine-functional compound as starting material. The amine-functional compound comprises at least two —NH— units of which at least one, in particular two (or more, if more are present), are selected from the group of primary amine groups and cyclic secondary amine groups. Cyclic secondary amine groups can be found in urea derivatives or piperazines. It is preferred in the amine-functional compound for the nitrogen atoms to be connected to each other via an ethylene chain (—CH2-CH2-), via a carbonyl group (—C(O)—), via two ethylene chains (thereby forming a piperazine ring), or via an ethylene chain and a carbonyl group (thereby forming a urea derivative).

Some examples of suitable amine-functional compounds are shown below as illustration. As will be clear to the skilled person, this can be extended to include pentamines, hexamines and so on.

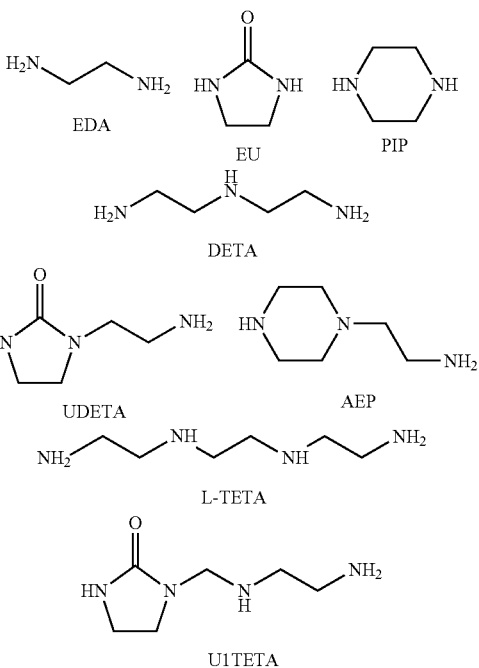

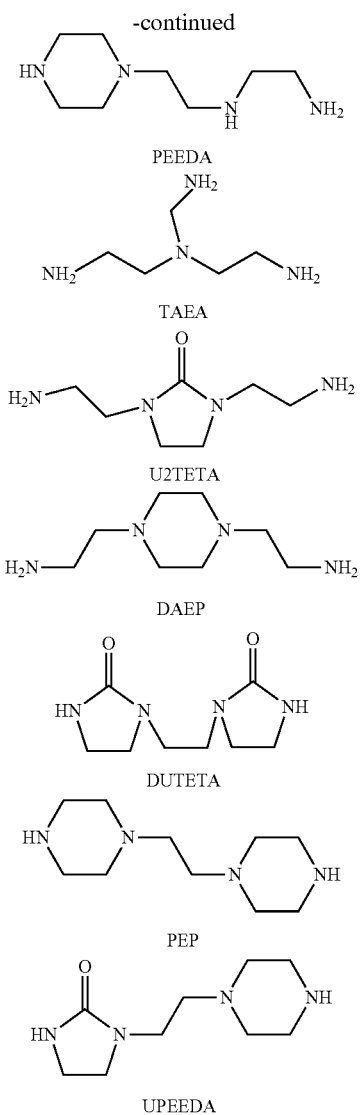

EDA Ethylene diamine
EU Ethylene urea
PIP Piperazine
DETA Diethylene triamine
UDETA Cyclic urea derivative of diethylenene triamine
AEP Aminoethyl piperazine
L-TETA Linear triethylene tetramine
U1TETA Cyclic urea derivative of triethylene tetramine, with the carbonyl group added to the terminal NH2-CH2-CH2-NH moiety
PEEDA Piperazinoethyl ethylene diamine
TAEA Trisaminoethylamine
U2TETA Cyclic urea derivative of triethylene tetramine, with the carbonyl group added to the central NH—CH2-CH2-NH moiety
DAEP Diaminoethyl piperazine
DUTETA Cyclic diurea additive of triethylene tetramine
PEP Piperazinoethyl piperazine
UPEEDA Cyclic urea derivative of piperazinoethyl ethylene diamine In one embodiment, the amine-functional compound comprises at least one —NH—CH2-CH2-NH— unit, wherein the —NH—CH2-CH2-NH— units in the amine-functional compound may be present in the form of a cyclic ethylene urea moiety or a piperazine moiety. EDA, EU, DETA and UDETA may be mentioned as preferred compounds. PIP and AEP may also be attractive. There may be a particular preference for EDA and EU.

In one embodiment, the amine-functional compound and the carbon oxide-delivering agent are at least partly added as one compound in the form of a urea adduct.

In the process according to the invention, the molar ratio of amine-functional compound to monoethylene glycol is 0.2:1 to 1.5:1. If the molar ratio of amine-functional compound to monoethylene glycol is below 0.2:1, the conversion to hydroxyethyl ethylene amines will be insufficient to obtain a commercially attractive process. If the ratio is low, e.g., in the range of 0.2:1 to 0.5:1, the main product may be di-hydroxylethylene amines. At higher ratios, e.g., above 0.5:1, more mono-hydroxyethylene amines will be formed. It may be preferred for the molar ratio of amine-functional compound to monoethylene glycol to be at least 0.7:1, in particular at least 0.8:1.

If the molar ratio of amine-functional compound to monoethylene glycol is above 1.5:1, a substantial part of the product hydroxyethyl ethylene amine may react further to form polyethylene polyamines, which is not the aim of the present invention. It may also be preferred for the molar ratio of amine-functional compound to monoethylene glycol compound to be at most 1.3:1, in particular at most 1.2:1.

In the process of the invention the molar ratio of carbon oxide-delivering agent to —NH—CH2-CH2-NH— units in the amine-functional compound is at least 0.5:1. If the value is below this range, the conversion will be too low. It is preferred for the molar ratio of carbon oxide-delivering agent to —NH—CH2-CH2-NH— units to be at least 0.7:1, or at least 0.9. It may be particularly preferred for the ratio to be at least 1:1.

The maximum ratio is not critical. An upper limit of 5:1 may be mentioned in general. A maximum ratio of 3:1 may be attractive in commercial operation.

Further, it has been found that an optimum yield can be obtained if the molar ratio of carbon oxide-delivering agent to —NH—CH2-CH2-NH— units in the amine-functional compound is selected to be between 0.7:1 and 3:1, in some embodiments between 0.9:1 and 2:1, specifically between 1:1 and 1.75:1.

In this context a —NH—CH2-CH2-NH— unit is a unit which can form an ethylene urea unit in the amine-functional compound. For example, ethylene diamine (NH2-CH2-CH2-NH2) contains one —NH—CH2-CH2-NH— unit. Diethylene triamine (NH2-CH2-CH2-NH—CH2-CH2-NH2) also contains one —NH—CH2-CH2-NH— unit, since the middle NH unit can be part of only one —NH—CH2-CH2-NH— unit. Triethylene tetramine (NH2-CH2-CH2-NH—CH2-CH2-NH—CH2-CH2-NH2) contains two —NH—CH2-CH2-NH— units.

In one embodiment, the CO-delivering agent also provides the monoethylene glycol, in the form of ethylene carbonate, as a whole or in part, and/or the CO-delivering agent also provides the amine-functional compound as a whole or in part. It may be preferred to add at least 50% of the CO in the form of either monoethylene glycol or in the form of the amine-functional compound, in particular at least 75%, more in particular at least 90%. In one embodiment, at least 95%, or essentially all, of the CO is added in the form of either monoethylene glycol or of the amine-functional compound.

In this case the maximum molar ratio of the CO-delivering compound to the number of ethylene groups present in the system as monoethylene glycol and —NH—CH2-CH2-NH— units in the amine-functional compound is 1:1.

In one embodiment, the reaction product comprises alkanolamines of the formula NH2-(CH2-CH2-NH)q-CH2-CH2-OH, wherein q has a value of 1-10, in particular 1-5, more in particular 1-3, preferably 1 or 2, and wherein one or more —NH—CH2-CH2-NH— units may be present as a cyclic ethylene urea unit

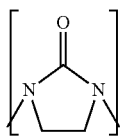

or piperazine unit,

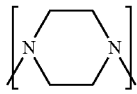

and wherein one or more —NH—CH2-CH2-OH units may be present as cyclic ethylene carbamate units

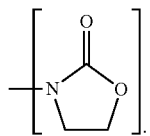

In one embodiment, one or more alkanol amines or derivatives thereof as specified above are connected to each other via a linear ethylene urea structure, e.g. as follows:

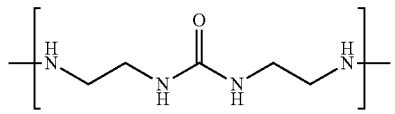

In one embodiment, the amine-functional compound comprises ethylene diamine (EDA), ethylene urea (EU), or a mixture thereof, and the reaction product comprises aminoethyl ethanolamine (AEEA) and/or urea and carbamate derivatives thereof.

In another embodiment, the amine-functional compound comprises diethylene triamine (DETA), the urea derivative thereof (UDETA), or a mixture thereof, and the reaction product comprises hydroxyethyl diethylene triamine (HEDETA) and/or urea and carbamate derivatives thereof.

It should be noted that the relative ratios between the various components are to be calculated based on the compounds monoethylene glycol, carbon dioxide, and amine-functional compound, irrespective of the form in which they are added. For example, one mole ethylene urea should be regarded as being equivalent to one mole carbon dioxide and one mole ethylene diamine. For another example, one mole of the diurea adduct of triethylene tetramine (DUTETA) should be regarded as being equivalent to two moles carbon dioxide-delivering agent and one mole triethylene tetramine.

The reaction is carried out by combining the various components and bringing the mixture to reaction conditions.

Reaction conditions include a reaction temperature which is generally at least 100° C. The temperature should preferably be lower than 400° C. More preferably, the temperature is between 200 and 360° C. Even more preferably, the temperature is between 240 and 340° C. Most preferably, the temperature is between 250 and 310° C. The reaction is carried out at a pressure which is such that the reaction mixture is in the liquid phase. It will therefore depend on the reaction temperature. In general, the reaction pressure will be between 1 and 60 bar.

The reaction time during the process in an embodiment is between 5 minutes and 40 hours, preferably between 0.5 and 10 hours, more preferably between 1 and 6 hours.

The process of the present invention can be performed with or without any additional liquid present. If a liquid is added to the reaction system, the liquid preferably is a polar liquid, such as an alcohol or water. Performing the process of the present invention in the presence of water as a liquid or without any additional liquid is preferred.

The reactor employed can be any suitable reactor including a continuously stirred tank reactor, pipeline reactor, tubular or multi-tubular reactor. The reactor may be adiabatic or equipped with external or internal heat exchanging devices. Feed may be single point or split into multiple points. It can consist of multiple stages with inter-stage heat exchange.

The process can be carried out in a batch reactor, possibly fed-batch operation, or in a continuously operating system in one reactor or in a cascade of continuous flow reactors. The reactor can be a single reaction unit or a set of reaction units. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

The product mixture can be further processed or fractionated into several products that each independently are either pure compounds or a mixture of compounds, some of which may be recycled.

The reaction product will comprise one or more compounds in the form of urea adducts. In one embodiment, the product is subjected to a hydrolysis reaction to convert the urea adduct into hydroxyethyl ethylene amine compounds.

The present invention will be elucidated by the following examples, without being limited thereto or thereby.

EXAMPLE 1: MEG+EDA+EU AT DIFFERENT CO:AMINE-FUNCTIONAL COMPOUND MOLAR RATIOS

Reaction mixtures were prepared comprising monoethylene glycol, ethylene diamine, and ethylene urea. The molar ratio between amine-functional compound (the total of ethylene diamine and ethylene urea) and monoethylene glycol was 1:1. The amount of ethylene urea was selected such that the molar ratio of CO to amine-functional compounds (EDA+EU) was at the value specified in the table, varying between 0.05:1 and 1.5:1. At ratios above 1:1 CO2 is provided to the reaction mixture.

The reaction mixtures were brought to a temperature of 270° C. under autogenous pressure, and allowed to react for 5 hours. After the reaction, the reaction mixtures comprised the following amount of (U)AEEA compounds, calculated in mole percentage based on the starting amount of MEG in moles.

| Experiment | 1.1 | 1.2 | 1.3 | 1.4 | 1.5 | 1.6 | 1.7 |
|---|---|---|---|---|---|---|---|
| CO:(EDA + EU) molar ratio | 0.05 | 0.3 | 0.7 | 0.9 | 1.0 | 1.25 | 1.5 |
| Σ(U)AEEA | 0.0 | 5.1% | 10.8% | 13.0% | 19.6% | 20.2% | 14.2% |

As can be seen from this data, a CO:(EDA+EU) ratio of 0.05:1 or 0.3:1 is insufficient to obtain a meaningful conversion to AEEA. At high CO:amine ratios (above 1.25:1), the yield of AEEA decreases.

The invention claimed is:

1. Process for preparing hydroxyethyl ethylene amines and/or ethylene urea derivatives thereof comprising the step of reacting monoethylene glycol with an amine-functional compound comprising at least two —NH— units of which at least one is selected from the group of primary amine groups and cyclic secondary amine groups, the amine-functional compound comprising at least one —NH—CH2-CH2-NH— unit, wherein one or more —NH-CH2-CH2-NH— units in the amine-functional compound may be present in the form of piperazine moieties of the formula

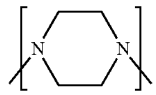

or ethylene urea moieties of the formula

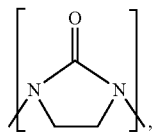

in the presence of a carbon oxide-delivering agent,
wherein the molar ratio of amine-functional compound to monoethylene glycol is in the range of 0.2:1 to 1.5:1,
wherein the molar ratio of carbon oxide-delivering agent to —NH-CH2-CH2-NH— units in the amine-functional compound is at least 0.5:1,
wherein a —NH-CH2-CH2-NH— unit is a unit which can form an ethylene urea unit in the amine-functional compound, and
wherein the carbon oxide delivering agent is selected from the group of carbon dioxide, the CO adduct of monoethylene glycol selected from the group of cyclic ethylene carbonate and HO-CH2-CH2-O—C(O)—O-CH2-CH2-OH, and urea-derivatives of ethylene amine compounds.

2. Process according to claim 1, wherein the carbon oxide-delivering agent is selected from the group of carbon dioxide and ethylene urea (EU) of the formula

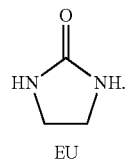

3. Process according to claim 1, wherein the molar ratio of amine-functional compound to monoethylene glycol is at least 0.5:1.

4. Process according to claim 1, wherein the molar ratio of carbon oxide-delivering agent to —NH-CH2-CH2-NH— units in the amine-functional compound is at least 0.7:1.

5. Process according to claim 4, wherein the molar ratio of carbon oxide-delivering agent to —NH-CH2-CH2-NH— units in the amine-functional compound is between 0.7:1 and 3:1.

6. Process according to claim 1, wherein at least 50% of CO added in the process is added in the form of a CO adduct of monoethylene glycol selected from the group of cyclic ethylene carbonate and HO-CH2-CH2-O—C(O)—O-CH2-CH2-OH, or in the form of urea-derivatives of ethylene amine compounds.

7. Process according to claim 1, wherein the reaction product comprises alkanolamines of the formula NH2-(CH2-CH2-NH)q-CH2-CH2-OH, wherein q has a value of 1-10, wherein one or more —NH-CH2-CH2-NH— units may be present as cyclic ethylene urea units or piperazine units, and/or linear ethylene urea units and wherein one or more —NH-CH2-CH2-OH units may be present as cyclic ethylene carbamate units, and wherein one or more alkanol amines or derivatives thereof can be connected to each other via a linear ethylene urea structure.

8. Process according to claim 1, wherein the amine-functional compound comprises ethylene diamine (EDA), ethylene urea (EU), or a mixture thereof, and the reaction product comprises aminoethyl ethanolamine (AEEA) and/or urea and carbamate derivatives thereof.

9. Process according to claim 1, wherein the molar ratio of amine-functional compound to monoethylene glycol is at least 0.8:1 and at most 1.2:1.

10. Process according to claim 1, wherein the molar ratio of carbon oxide-delivering agent to —NH-CH2-CH2-NH— units in the amine-functional compound is at least 1:1 and at most 3:1.

11. Process according to claim 10, wherein the molar ratio of carbon oxide-delivering agent to —NH-CH2-CH2-NH— units in the amine-functional compound is between 1:1 and 1.75:1.

12. Process according to claim 1, wherein essentially all of CO added in the process is added in the form of a CO adduct of monoethylene glycol selected from the group of cyclic ethylene carbonate and HO-CH2-CH2-O—C(O)—O-CH2-CH2-OH, or in the form of urea-derivatives of ethylene amine compounds.

13. Process according to claim 1, wherein the reaction product comprises alkanolamines of the formula NH2-

(CH2-CH2-NH)q-CH2-CH2-OH, wherein q has a value of 1 or 2, wherein one or more —NH-CH2-CH2-NH— units may be present as cyclic ethylene urea units or piperazine units, and/or linear ethylene urea units and wherein one or more —NH-CH2-CH2-OH units may be present as cyclic ethylene carbamate units, and wherein one or more alkanol amines or derivatives thereof can be connected to each other via a linear ethylene urea structure.

14. Process according to claim 1, wherein the reaction product comprises alkanolamines of the formula NH2-(CH2-CH2-NH)q-CH2-CH2-OH, wherein q has a value of 1-10, wherein one or more —NH-CH2-CH2-NH— units may be present as linear ethylene urea units of the formula

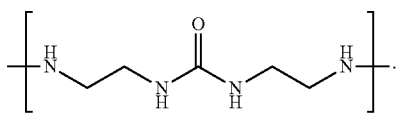

15. Process according to claim 1, wherein the reaction product comprises alkanolamines of the formula NH2-(CH2-CH2-NH)q-CH2-CH2-OH, wherein q has a value of 1-10, wherein one or more —NH-CH2-CH2-OH units may be present as cyclic ethylene carbamate units of the formula

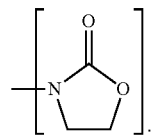

* * * * *